United States Patent [19]

Kaplan et al.

[11] Patent Number: 4,990,158

[45] Date of Patent: Feb. 5, 1991

[54] SYNTHETIC SEMIABSORBABLE TUBULAR PROSTHESIS

[75] Inventors: Donald S. Kaplan, Weston; John Kennedy, Stratford; Ross R. Muth, Brookfield, all of Conn.

[73] Assignee: United States Surgical Corporation, Norwalk, Conn.

[21] Appl. No.: 349,648

[22] Filed: May 10, 1989

[51] Int. Cl.⁵ ............................................. A61F 2/06
[52] U.S. Cl. ........................................... 623/1; 57/225
[58] Field of Search ........................ 57/225, 226, 12; 606/230, 228; 623/11, 12, 1

[56] References Cited

U.S. PATENT DOCUMENTS

| | | |
|---|---|---|
| 3,463,158 | 8/1969 | Schmitt et al. . |
| 3,537,280 | 4/1970 | Garrov et al. ................. 57/225 X |
| 3,688,317 | 9/1972 | Kurtz ................................ 623/1 |
| 3,805,300 | 4/1974 | Tascon-Alonso et al. . |
| 3,878,565 | 4/1975 | Sauvage . |
| 4,047,252 | 9/1977 | Liebig et al. . |
| 4,187,558 | 2/1980 | Dahlen et al. . |
| 4,193,138 | 3/1980 | Okita . |
| 4,208,745 | 6/1980 | Okita . |
| 4,229,838 | 10/1980 | Mano . |
| 4,286,341 | 9/1981 | Greer et al. . |
| 4,301,551 | 11/1981 | Dore et al. . |
| 4,340,091 | 7/1982 | Skelton et al. ....................... 623/1 |
| 4,350,731 | 9/1982 | Siracusano . |
| 4,378,017 | 3/1983 | Kosugi et al. . |
| 4,467,595 | 8/1984 | Kramers ........................... 57/225 |
| 4,474,851 | 10/1984 | Urry . |
| 4,483,023 | 11/1984 | Hoffman, Jr. et al. . |
| 4,518,687 | 5/1985 | Liebig et al. . |
| 4,530,113 | 7/1985 | Matterson . |
| 4,584,722 | 4/1986 | Levy et al. . |
| 4,610,688 | 9/1986 | Silvestrini et al. . |
| 4,621,638 | 11/1986 | Silvestrini ...................... 606/230 |
| 4,624,256 | 11/1986 | Messier et al. ................. 606/230 |
| 4,642,119 | 2/1987 | Shah . |
| 4,663,221 | 5/1987 | Makimura et al. . |
| 4,693,720 | 9/1987 | Scharnberg et al. ............. 623/11 |
| 4,713,070 | 12/1987 | Mano . |
| 4,713,075 | 12/1987 | Kurland ...................... 606/230 X |
| 4,718,907 | 1/1988 | Karwoski et al. . |
| 4,788,979 | 12/1988 | Jarrett et al. . |
| 4,792,336 | 12/1988 | Hlavacek et al. . |
| 4,816,028 | 3/1989 | Kapadia et al. . |
| 4,816,339 | 3/1989 | Tu et al. . |
| 4,822,361 | 4/1989 | Okita et al. . |
| 4,871,365 | 10/1989 | Dumican . |

FOREIGN PATENT DOCUMENTS

| | | |
|---|---|---|
| 0169045 | 1/1986 | European Pat. Off. . |
| 0202444 | 11/1986 | European Pat. Off. . |
| 0239775 | 10/1987 | European Pat. Off. . |
| 0241252 | 10/1987 | European Pat. Off. . |
| WO84/00302 | 2/1984 | World Int. Prop. O. . |
| WO89/01320 | 2/1989 | World Int. Prop. O. . |

*Primary Examiner*—Alan W. Cannon
*Attorney, Agent, or Firm*—Thomas R. Bremer; Peter G. Dilworth; Rocco S. Barrese

[57] ABSTRACT

A composite yarn possessing a nonabsorbable, elastic core yarn component and an absorbable, relatively inelastic sheath yarn component is employed in the manufacture of a porous tubular prosthesis useful, e.g., in vascular reconstruction.

38 Claims, 1 Drawing Sheet

SYNTHETIC SEMIABSORBABLE TUBULAR PROSTHESIS

BACKGROUND OF THE INVENTION

This invention relates to the fields of composite yarns, fabrics manufactured therefrom and to tubular, e.g., vascular tissue, prostheses manufactured from yarns or fabrics.

At present there are two surgical methods used in vascular repair. In one method, human tissue is harvested, usually from the patient, and then re-implanted. This necessitates two operations and the difficult handling of tissue. In the other method, vascular repair is achieved with a synthetic tubular prosthesis made from a non-absorbing material such as Dacron (DuPont's synthetic polyester fiber made from polyethyleneterephthalate) or polytetrafluoroethylene (PTFE). These grafts are permanent and sometimes show failure after extended service due to their dissimilarity to natural tissue. These grafts are also limited to repair of larger vessels because of occlusion. Grafts with minimal porosity do not bleed but also do not allow tissue ingrowth. Grafts with high porosity allow tissue ingrowth and formation of a neointimal surface contact with the blood, however, these grafts must be pre-clotted in the patient's blood prior to placement. Some porous grafts with coatings such as albumin have been developed in the hope of encouraging tissue ingrowth.

According to U.S. Pat. No. 4,474,851, the most commonly used fabric for blood vessel prosthesis is made from Dacron produced in several weaves and in combination with other materials. An example of such a material is the DeBakey Elastic Dacron fabric manufactured by USCI, a division of C. R. Bard, Inc. (Cat. No. 007830). Other commonly used materials are said to include felted polyurethane and polytetrafluoroethylene (Berkowitz et al., *Surgery*, 72, 221 (1972); Wagner et al., J. Surg. Res., 1, 53 (1956); Goldfarb et al., *Trans. Am. Soc. Art. Int. Org.*, XXIII, 268 (1977)). However, it is noted that none of these materials even when specially woven or crimped is able to satisfactorily simulate the elastic nature of natural blood vessel walls (Takabayashi et al., *J. Surg. Res.*, 19, 209 (1975)). Because of this, blood pressure response and blood flow occur differently in natural and artificial blood vessels, and the desirable normal flow characteristics and pressure response are not attained Changes in blood flow are undesirable and often lead to clotting For disclosures of various known types of vascular prostheses, reference may be made to U.S. Pat. Nos. 4,208,745 and 4,713,070 (PTFE); 4,378,017 (de-N-acetylated chitin and fibrous collagen); 4,474,851 (composite yarn possessing an artificial core fiber, e.g., a polyester such as Dacron, and an elastomeric polypeptide chemically bonded to the surface of the core fiber); 4,718,907 (cross-linked fluorine-containing polymer coatings on a substrate, e g., a fabric manufactured from polyethylene terephthalate); European Patent Application No. 0 202 444 (fibers manufactured from an absorbable polymer, e.g., one derived from trimethylene carbonate, and fibers manufactured from a nonabsorbable polymer, e.g., Hytrel or polyethylene terephthalate); and, PCT Patent Publication No. WO 84/00302 (polylactic acid and segmented polyester urethane or polyether urethane solution deposited upon a PTFE substrate). PCT Patent Publication No. WO 89/01320 describes a soft tissue prosthesis, said to be useful as a vascular tissue replacement, which as a ligament prosthesis possesses a central region made up of a core component comprising a parallel array of elastomeric yarns, e.g., of a spandex-type polyurethane/urea/ether block copolymer, preferably wrapped with layers of Dacron.

SUMMARY OF THE INVENTION

In accordance with the present invention, there is provided a synthetic, semiabsorbable composite yarn comprising a nonabsorbable, elastic core yarn which imparts resiliency to the composite yarn, the core yarn being covered with an absorbable, relatively inelastic sheath yarn which imparts transverse tensile strength to the composite yarn.

The invention also provides a fabric which is manufactured from said composite yarn and a tubular prosthesis exhibiting staged bioabsorption of its external surfaces which is manufactured from the fabric or directly from the composite yarn.

The tubular prosthesis of the present invention overcomes or minimizes one or more of the drawbacks associated with known vascular prostheses such as those referred to above. Thus, the porous structure which develops in the prosthesis as its external surfaces are eroded by bioabsorption provides an effective scaffold for tissue ingrowth while the combination of nonabsorbable elastic core and absorbable inelastic sheath yarns of the individual composite yarns from which the prosthesis is manufactured provides initial strength and, with the absorption of its external surfaces, exhibits structural properties resembling the dynamic fluid pressure response characteristics of natural vascular tissue.

DESCRIPTION OF THE PREFERRED EMBODIMENTS

Figure 1:
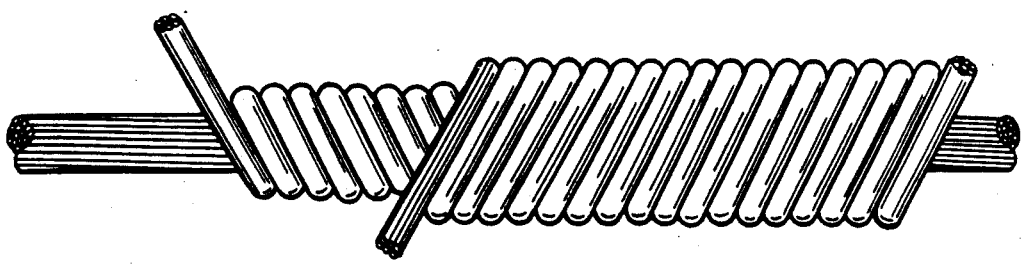
FIGS. 1 and 2 are enlarged isometric view of composite yarn constructed in accordance with the present invention.
Figure 2:
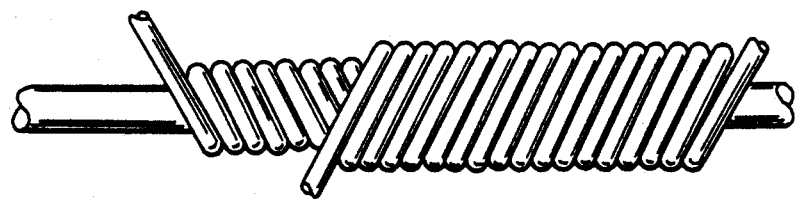
Figure 3:
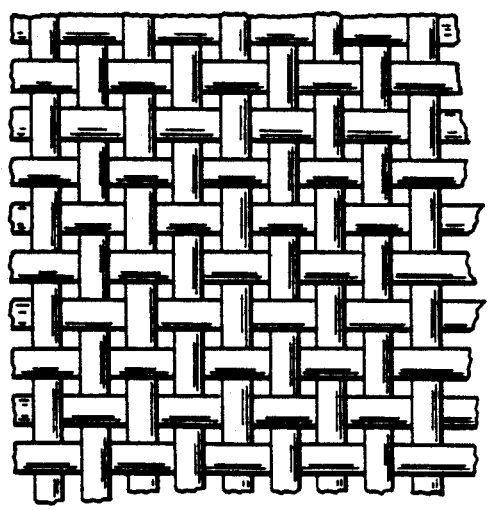
FIG. 3 is an enlarged plan view of a section of fabric woven from the composite yarn of FIG. 1; and, FIG. 4 represents a section of a tubular prosthesis, suitable, e.g., in vascular or tracheal reconstruction, which is manufactured from the composite yarn of FIG. 1.

As shown in FIG. 1, composite yarn 10 comprises a core yarn component 12 made up of a multiplicity of individual nonabsorbable elastic filaments 13, advantageously provided with a slight to moderate twist, and an internal sheath yarn component 14 made up of a multiplicity of individual absorbable, relatively inelastic filaments 15 wound in a first direction about the core and an external multifilamentous sheath yarn component 16, also made up of individual absorbable, relatively inelastic filaments 17, wound in a second, opposite direction about sheath yarn 14. Core yarn 12 functions to impart resiliency to composite yarn 10 while sheath yarns 14 and 16 function to impart tensile strength to the composite yarn. Sheath yarns 14 and 16 each has a lengthwise axis which is non-perpendicular to the lengthwise axis of core 12. While core yarn 12 can be wrapped with a single layer of sheath yarn, the illustrated arrangement of two layers of sheath yarns 14 and 16 is generally preferred as this construction helps to give composite yarn 10 a balanced structure which resists crimping or kinking when used in the manufacture of a fabric or prosthesis such as shown in FIGS. 2 and 3. Where, as shown in the embodiment of FIG. 1, at least two sheath yarns are employed in the construction of the composite yarn, the composition of these yarns as well as their relative rates of absorption can differ. This capability for differential absorption can be advantageously exploited in a vascular prosthesis article in which the outermost sheath yarn is absorbed by the body at a faster rate than the underlying sheath yarn thus resulting in a staged absorption of the sheath component of the composite yarn.

The term "elastic" as applied to core 12 herein shall be understood to refer to a polymer which in filamentous form exhibits a relatively high degree of reversible extensibility, e.g., an elongation at break of at least about 30%, preferably at least about 40% and more preferably at least about 50%.

In addition to the quality of being elastic core yarn 12 must also be nonabsorbable, i.e., it must resist chemical degradation when, as part of a tubular prosthesis, it is implanted in a body. Fiber-forming polymers which satisfy these essential requirements of the core yarn component of composite yarn 10 include fiber-forming polyolefins such as polyethylene homopolymers, polypropylene homopolymers, ethylene propylene copolymers, ethylene propylene terpolymers, etc., fluorinated hydrocarbons, fluorosilicones, isobutylene isoprenes, polyacrylates, polybutadienes, polyurethanes, polyetherpolyester copolymers, and the like. Hytrel (DuPont), a family of copolyester elastomers based on (soft) polyether segments and (hard) polyester segments, and spandex, an elastomeric segmented polyurethane, provide especially good results.

If desired, the core yarn can be provided with a nonabsorbable hydrophilic coating to improve its wettability by body fluids, e.g., blood. Hydrophilic coatings which are suitable for this purpose include polymeric materials such as the sparingly crosslinked poly(hydroxyethyl methacrylate) hydrogels disclosed in U.S. Pat. Nos. 2,976,576 and 3,220,960; hydrogels based on cross-linked polymers of n-vinyl lactams and alkyl acrylates as disclosed in U.S. Pat. No. 3,532,679; graft copolymers of hydroxyalkyl methacrylate and polyvinylpyrrolidone disclosed in U.S. Pat. No. 3,621,079, and many others.

Yarns manufactured from materials which are not elastic in the foregoing sense can be regarded as "relatively inelastic" as that expression is used in connection with the sheath yarn component of the composite fiber of this invention and, provided such relatively inelastic materials are absorbable within the body, are suitable for providing the sheath yarn. It is to be understood, however, that the expression "relatively inelastic" does not preclude the presence of some minor degree of elasticity in the sheath yarn, merely that it excludes a degree of elasticity in such yarn which is more characteristic of the core yarn.

The sheath yarn will ordinarily possess a relatively high tensile strength, e.g., a straight tensile strength of at least about 30,000 p.s.i., preferably at least about 60,000 p.s.i. and more preferably at least about 90,000 p.s.i.

Absorbable, inelastic fiber-forming polymers and polymer blends from which the sheath yarn herein can be formed include those derived at least in part from such monomers as glycolic acid, glycolide, lactic acid, lactide, p-dioxanone, trimethylene carbonate, e-caprolactone, hydroxycaproic acid, etc., and various combinations of these and related monomers as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,052,988; 4,060,089; 4,137,921; 4,157,437; 4,234,775; 4,237,920; 4,300,565; 4,429,080; 4,441,496; 4,523,591; 4,546,152; 4,559,945; 4,643,191; 4,646,741; 4,653,497; and, 4,741,337; U.K. Patent No. 779,291; D.K. Gilding et al., "Biodegradable polymers for use in surgery—polyglycolide/poly(lactic acid) homo- and copolymers 1, *Polymer*, Volume 20, pages 1459–1464 (1979), and D. F. Williams (ed.), *Biocompatibility of Clinical Implant Materials*, Vol. II, ch. 9: "Biodegradable Polymers" (1981).

Sheath yarns manufactured from polymers of high lactide or glycolide content, e.g., those in which at least about 75% of the monomeric units are derived from either glycolide or lactide, are preferred for the construction of the sheath yarn component of the composite yarn of this invention. Polymers of high glycolide content tend to be absorbed more quickly than those possessing a high lactide content. Accordingly, the glycolide-based polymers may be preferred for the manufacture of a sheath yarn providing the outermost sheath yarn in a multiple sheath yarn construction, the underlying internal sheath yarn(s) being manufactured from the more slowly absorbable lactide-based polymers.

The deniers of core yarn 12 and sheath yarns 14 and 16 are not especially critical with commercially available deniers being suitably employed. Preferably, such deniers are selected so as to provide a composite yarn having an overall denier of from about 40 to about 1200 and preferably from about 80 to about 400, the overall denier of the core and/or sheath yarns being from about 20 to about 600 and preferably from about 40 to about 200. The deniers of individual filaments in the core and sheath yarns of multifilamentous construction can vary widely, e.g., from about 0.2 to about 6.0 and preferably from about 0.4 to about 3.0. The base weight for a desired composite yarn will determine the size and weight of the component elements of the yarn. Composite yarn 10 possesses sufficient core material to impart a desired resiliency and sufficient sheath material to provide a desired tensile strength for a prosthetic application. In general, the core component can represent from about 20 to about 80%, and preferably from about 30 to about 70%, of the total weight of the composite yarn 10. Optimum core and sheath weights will, of course, vary depending on the specific application of the composite yarn and can be readily determined in a given case by simple trial-and-error technique without undue experimentation.

Methods and apparatus for covering core yarns with sheath yarns are well known and need not be described here in detail. In general, the sheath yarns are wrapped about the core yarn on a covering machine which includes a hollow spindle with rotating yarn supply bobbins supported thereon The elastic core yarn is fed through the hollow spindle and the elastic sheath yarns are withdrawn from the alternate direction rotating supply bobbins and wrapped about the core yarn as it emerges from the hollow spindle. The core yarn is preferably under a slight tension during the covering procedure and the sheath yarns are laid down in a side-by-side array. The number of wraps per inch will depend on the denier of the sheath yarns but should be sufficient to cause the sheath yarns to lay close to the core yarn when tension on the latter is relaxed.

As desired, the sheath yarns can be provided with no twist or with varying degrees of twist. Where the yarns are twisted, it can be advantageous to balance or equalize the twist in the final composite yarn structure. Thus, for example, in the embodiment of composite yarn 10, if sheath yarn 14 has a given twist, sheath yarn 16 should have an equivalent twist Since sheath yarns 14 and 16 are laid down in opposite directions, the twist in each of these yarns will be neutralized in the final structure of the composite yarn. Similarly, sheath yarns 14 and 16 are advantageously of about equal weight in order to provide further balance in the composite yarn.

The composite yarn 20 shown in FIG. 2 is similar to that of FIG. 1 except that core yarn component 22 constitutes a monofilament and internal and external sheath yarns 24 and 26, respectively, each constitutes a monofilament. In all other structural and compositional respects, composite yarn 20 can be like that of composite yarn 10.

Figure 4:
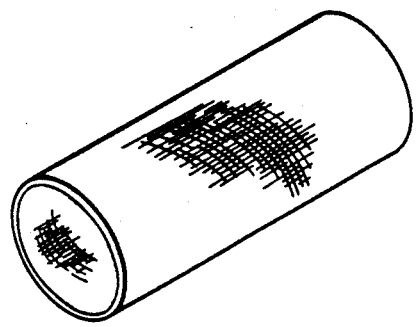
Figure 1:
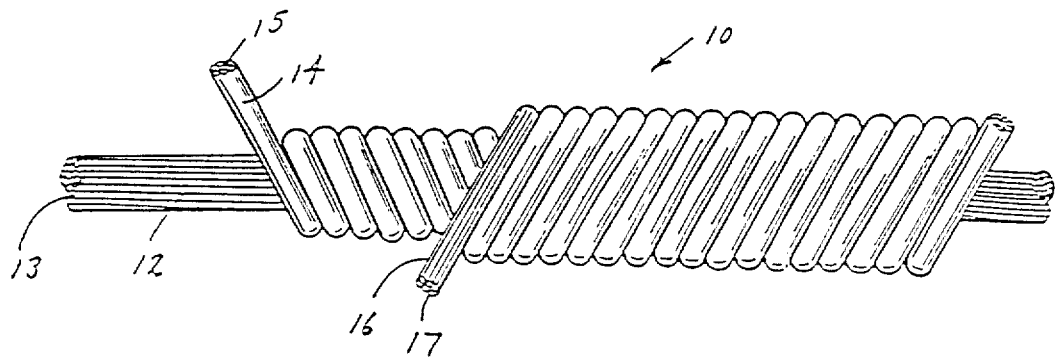
Figure 2:
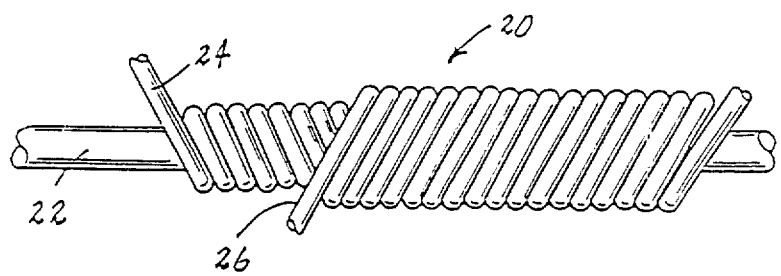
Figure 3:
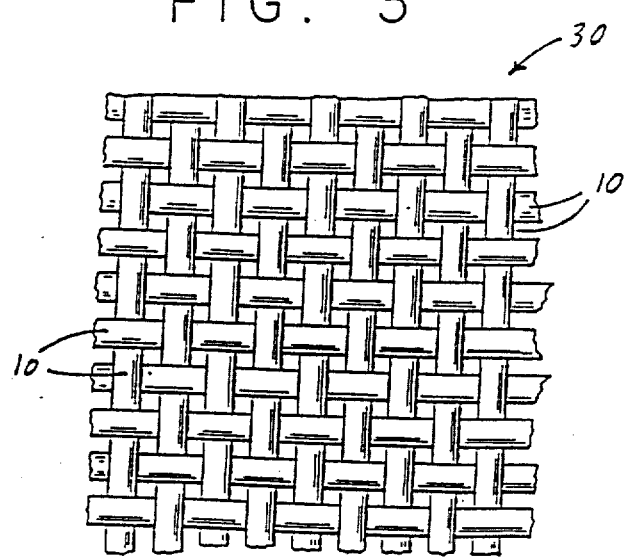
Figure 4:
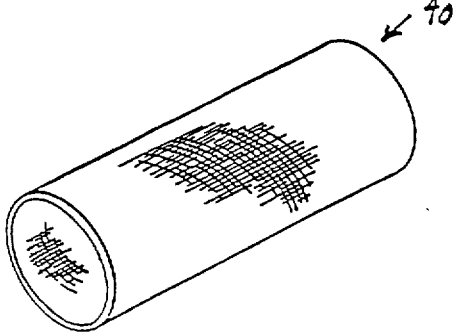

FIG. 3 is an enlarged plan view of a fabric 30 manufactured from warp and filling composite yarns 10 of FIG. 1. A simple construction is shown but those skilled in the art will appreciate that fabric 30 can be of complex construction or, for that matter, any known or conventional construction used in the manufacture of fabric. The ends of fabric 30 can be formed into tubular prosthesis 40 of FIG. 4 by conventional seam joining. Alternatively and preferably, fabric 30 can be formed into tubular structure 40 by weaving, braiding or knitting on a known or conventional loom thus eliminating the need for a seam. Tubular prosthesis 40 can, if desired, be given a crimped surface to increase its radial strength and/or can be provided with an external support component, e.g., a helical wrapping, for the same purpose.

At least one surface of fabric 30 and tubular prosthesis 40 is coated with an elastomeric absorbable material which temporarily renders these otherwise porous articles impervious to blood and/or other body fluid. This coating material is gradually absorbed into the body to be replaced by new tissue which maintains the liquid-impervious character of the prosthesis. As previously mentioned, the sheath component of the individual composite yarns from which the fabric/tubular prosthesis is manufactured will itself erode over time due to its bioabsorption leaving only the nonabsorbable core as a permanent scaffold for the new tissue growth. The degree of elasticity exhibited by the absorbable coating material must be sufficient to accommodate the alternate elongation-contraction which the fabric/tubular prosthesis undergoes when implanted in the body while at the same time retaining its fluid-occluding function.

This sequence of stepped, or staged, absorption of the outer elastomeric absorbable coating followed by absorption of the underlying absorbable sheath yarns (themselves capable of staged bioabsorption in an embodiment previously described) occurring over an extended period of time and accompanied by a gradual accumulation of new tissue which replaces the absorbed components enables the prosthetic article of this invention to remaining impervious to blood and other body fluids while providing an effective support structure for new tissue.

Suitable elastomeric absorbable coating materials include those prepared from such monomers as glycolic acid, glycolide, lactic acid, lactide, p-dioxanone, trimethylene carbonate, e-caprolactone, hydroxycaproic acid, etc., and optionally can contain one or more blocks or sequences of polymeric units which are hydrophiliic in character, e.g., poly(oxyalkylene) units such as poly(oxyethylene), poly(oxypropylene), poly(oxyethylene-oxypropylene), etc. Thus, e.g., a suitable absorbable elastomeric coating can be based on a terpolymer of polyethylene glycol, e-caprolactone and glycolide and can be applied to the fabric/tubular prosthesis from solution, e.g., of acetone, methylene chloride or other suitable organic solvent. The quantity of elastomeric absorbable coating required to achieve fluid imperviousness in the underlying fabric/tubular prosthesis will vary in accordance with the structure and mechanical properties of the particular substrate material being coated. In general, the coating can represent from 0.1 to about 5%, and preferably from about 0.2 to about 3%, by weight of the entire coated structure.

It is also within the scope of this invention to coat or impregnate tubular prosthesis 40 with, or otherwise apply thereto, one or more materials which enhance its functionality. For example, an anti-thrombogenic material such as heparin can be incorporated into the prosthesis, advantageously by addition to the absorbable elastomeric coating composition which is applied to the prosthesis.

It is also within the scope of the invention to incorporate into the prosthesis one or more medicosurgically useful substances, e.g., those which accelerate or beneficially modify the healing process when the prosthesis is applied to a graft site. So, for example, the prosthesis can be provided with a therapeutic agent which will be deposited at the grafted site. The therapeutic agent can be chosen for its antimicrobial properties, capability for promoting wound repair and/or tissue growth or for specific indications such as thrombosis. Thus, for example, antimicrobial agents such as broad spectrum antibiotics (gentamycin sulphate, erythromycin or derivatized glycopeptides) which are slowly released into the tissue can be incorporated into the prosthesis to aid in combating clinical and sub-clinical infections in a surgical or trauma wound site. To promote wound repair and/or tissue growth, one or several growth promoting factors can be introduced into the tubular prosthesis, e.g., fibroblast growth factor, platelet derived growth factor, macrophage derived growth factor, alveolar derived growth factor, monocyte derived growth factor, magainin, and so forth. In all cases, the amounts of these functional additives can be within the usual art-recognized ranges.

What is claimed is:

1. A synthetic, semiabsorbable composite yarn which comprises:
    (a) a nonabsorbable, elastic core yarn imparting resiliency to the composite yarn; and,
    (b) at least one absorbable, relatively inelastic sheath yarn imparting transverse strength to the composite yarn.

2. The composite yarn of claim 1 in which the core yarn comprises one or multiple filaments.

3. The composite yarn of claim 1 in which the core yarn comprises twisted or intertwined multiple filaments.

4. The composite yarn of claim 3 in which the denier of an individual filament is from about 0.2 to about 6.0.

5. The composite yarn of claim 3 in which the denier of an individual filament is from about 0.4 to about 3.0.

6. The composite yarn of claim 1 in which the core yarn is manufactured from at least one polymeric material selected from the group consisting of ethylene homopolymer, propylene homopolymer, ethylene propylene copolymers, ethylene propylene terpolymers, fluorinated hydrocarbons, fluorosilicones, isobutylene isoprenes, polyacrylates, polybutadienes, polyurethanes, and polyetherpolyester copolymers.

7. The composite yarn of claim 1 in which the core yarn possesses an elongation at break of at least about 30%.

8. The composite yarn of claim 1 in which the core yarn possesses an elongation at break of at least about 40%.

9. The composite yarn of claim 1 in which the core yarn possesses an elongation at break of at least about 60%.

10. The composite yarn of claim 1 in which the sheath yarn is manufactured from an absorbable, relatively inelastic polymeric material derived at least in part from a monomer selected from the group consisting of glycolic acid, glycolide, lactic acid, lactide, p-dioxanone, trimethylene carbonate, e-caprolactone and hydroxycaproic acid.

11. The composite yarn of claim 1 in which the sheath yarn possesses a straight tensile strength of at least about 30,000 p.s.i.

12. The composite yarn of claim 1 in which the sheath yarn possesses a straight tensile strength of at least about 60,000 p.s.i.

13. The composite yarn of claim 1 in which the sheath yarn possesses a straight tensile strength of at least about 90,000 p.s.i.

14. The composite yarn of claim 1 in which the overall denier of the core yarn and/or sheath yarn is from about 20 to about 600 and the overall denier of the composite yarn is from about 40 to about 1200.

15. The composite yarn of claim 1 in which the overall denier of the core yarn and/or sheath yarn is from about 40 to about 200 and the overall denier of the composite yarn is from about 80 to about 400.

16. The composite yarn of claim 1 wherein the core yarn represents from about 20% to about 80% of the total weight of the composite yarn.

17. The composite yarn of claim 1 wherein the core yarn represents from about 30% to about 80% of the total weight of the composite yarn.

18. The composite yarn of claim 1 in which a sheath yarn is wound about the core yarn in direct contact therewith.

19. The composite yarn of claim 1 in which a first sheath yarn is helically wound around the core yarn in a first direction.

20. The composite yarn of claim 19 in which a second sheath yarn is helically wound around the first sheath yarn in a second, opposite direction.

21. The composite yarn of claim 20 in which the second sheath yarn exhibits a higher rate of absorbability than the first sheath yarn.

22. The composite yarn of claim 1 wherein a hydrophilic coating is applied to the core yarn.

23. A fabric manufactured from the composite yarn of claim 1, the fabric possessing a body fluid-impervious coating of an elastomeric absorbable material applied to at least one surface thereof.

24. The fabric of claim 23 in which the elastomeric absorbable material is a polymer derived at least in part from the group consisting of glycolic acid, glycolide, lactic acid, lactide, p-dioxanone, trimethylene carbonate, e-caprolactone and hydroxycaproic acid.

25. The fabric of claim 24 in which the polymer contains at least one hydrophilic sequence in the backbone thereof.

26. The fabric of claim 25 in which the hydrophilic sequence is selected from the group consisting of poly(oxyethylene), poly(oxypropylene) and poly(oxyethylene-oxypropylene).

27. The fabric of claim 23 which is woven, braided or knitted.

28. A tubular prosthesis manufactured from the composite yarn of claim 1, the tubular prosthesis possessing a body fluid-impervious coating of an elastomeric absorbable material applied to at least one surface thereof.

29. The tubular prosthesis of claim 28 in which the elastomeric absorbable material is a polymer derived at least in part from the group consisting of glycolic acid, glycolide, lactic acid, lactide, p-dioxanone, trimethylene carbonate, e-caprolactone and hydroxycaproic acid.

30. The tubular prosthesis of claim 29 in which the polymer contains at least one hydrophilic sequence in the backbone thereof.

31. The tubular prosthesis of claim 30 in which the hydrophilic sequence is selected from the group consisting of poly(oxyethylene), poly(oxypropylene) and poly(oxyethylene-oxypropylene).

32. The tubular prosthesis of claim 28 which is woven, braided or knitted.

33. The tubular prosthesis of claim 28 containing at least one medico-surgically useful substance.

34. The tubular prosthesis of claim 28 containing at least one anti-thrombogenic substance.

35. The tubular prosthesis of claim 34 in which the anti-thrombogenic substance is heparin.

36. A tubular prosthesis manufactured from the composite yarn of claim 18, the tubular prosthesis possessing a body fluid-impervious coating of an elastomeric absorbable material applied to at least one surface thereof.

37. The composite yarn of claim 1 in which a sheath yarn comprises one or multiple filaments.

38. The composite yarn of claim 1 in which a sheath yarn comprises twisted or intertwined multiple filaments.

* * * * *

UNITED STATES PATENT AND TRADEMARK OFFICE
CERTIFICATE OF CORRECTION

PATENT NO. : 4,990,158

DATED : February 5, 1991

INVENTOR(S) : Kaplan et al.

It is certified that error appears in the above-identified patent and that said Letters Patent is hereby corrected as shown below:

The Drawing Sheet, consisting of FIGS. 1-4, should be deleted and replaced with the attached Drawing Sheet which bears reference numerals.

Signed and Sealed this

Twenty-eighth Day of July, 1992

Attest:

DOUGLAS B. COMER

Attesting Officer

Acting Commissioner of Patents and Trademarks